United States Patent [19]

Sinha et al.

[11] Patent Number: 6,084,097
[45] Date of Patent: Jul. 4, 2000

[54] METHODS FOR PREPARING 1-[4-ARYLPIPERAZIN-1-YL]-3-[2-OXOPYRROLIDIN/PIPERIDIN-1-YL] PROPANES

[75] Inventors: Neelima Sinha; Sanjay Jain; Anil Kumar Saxena; Nitya Anand; Ram Mohan Saxena; Mangal Prasad Dubey; Madhur Ray, all of Lucknow; Gyanendra Kumar Patnaik, deceased, late of Lucknow, all of India, by Psuhpa Patnaik, Hemant Kumar Patnaik, Sumeet Patnaik, heirs

[73] Assignee: Council of Scientific & Industrial Research, New Delhi, India

[21] Appl. No.: 08/960,335

[22] Filed: Oct. 29, 1997

Related U.S. Application Data

[63] Continuation-in-part of application No. 08/954,516, Oct. 20, 1997.

[51] Int. Cl.[7] ............... C07D 401/06; C07D 401/14; C07D 403/06
[52] U.S. Cl. ............... 544/360; 544/364; 544/372
[58] Field of Search ................... 544/360, 364, 544/372

[56] References Cited

U.S. PATENT DOCUMENTS

| | | | |
|---|---|---|---|
| 4,273,712 | 6/1981 | Williams, III | 548/461 |
| 4,524,206 | 6/1985 | New et al. | 544/230 |
| 4,745,117 | 5/1988 | Ishizumi et al. | 514/254 |
| 5,077,295 | 12/1991 | Bright et al. | 514/254 |
| 5,599,815 | 2/1997 | Fukuda et al. | 514/254 |

*Primary Examiner*—Emily Bernhardt
*Attorney, Agent, or Firm*—Pennie & Edmonds LLP

[57] ABSTRACT

The invention relates to a process for the synthesis of 1-[4-Arylpiperazin-1-yl]-3-[2-oxopyrrolidin/piperidin-1-yl] propanes used as potential therapeutic agents for hypertension, ischemia, cardiovascular and other adrenergic receptors related disorders, having general formula 1

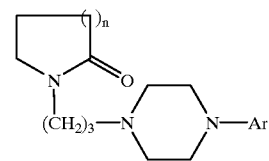

wherein Ar represents a phenyl ring substituted by the groups like halo, alkoxy, alkyl or heteroaryl, n=1 or n=2; a process of preparing said compounds and a method of treating hypertension, ischemia, cardiovascular and other adrenergic receptors related disorders.

8 Claims, 4 Drawing Sheets

X = O, S

METHODS FOR PREPARING 1-[4-ARYLPIPERAZIN-1-YL]-3-[2-OXOPYRROLIDIN/PIPERIDIN-1-YL] PROPANES

CROSS-REFERENCE TO RELATED APPLICATIONS

This application is a continuation-in-part application of application Ser. No. 08/954,516, filed Oct. 20, 1997, now pending.

FIELD OF INVENTION

The present invention relates to new 1-[4-Arylpiperazin-1-yl]-3-[2-oxopyrrolidin-1-yl]propanes and 1-[4-Arylpiperazin-1-yl]-3-[2-oxopiperidin-1-yl]propanes which can be used as therapeutic agents for hypertension, ischemia, cardiovascular and other adrenergic receptors related disorders, and a process for preparing said novel compounds. More, particularly the present invention relates to 1-[4-Arylpiperazin-1-yl]-3-[2-oxopyrrolidin-1-yl]propanes and 1-[4-Arylpiperazin-1-yl]-3-[2-oxopiperidin-1-yl]propanes, processes for preparing the said compounds and to their use in medicine.

Accordingly, the present invention provides compounds of formula 1.

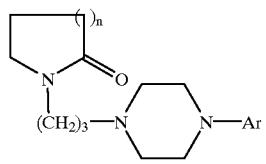

1

Wherein Ar represents a heteroaryl ring, or a phenyl ring substituted with a halogen, alkoxy, or alkyl and n=1 or n=2.

The compounds of the invention have shown to possess antihypertensive activity in different test models. The compounds also prevent post-ischemic reperfusion injury and may be useful in the treatment of hypertension, diseases arising out of alterations/impairment in central/peripheral circulations and adrenergic receptors systems, such as myocardial ischemia, myocardial infarction (MI), angina pectoris, any cardiac surgical interventions renal ischemia, circulatory insufficiency in extremities, stroke and trauma.

A method of preparation of the inventive compounds starts from the condensation of 1-bromo-3-chloropropane with 2-pyrrolidone or 2-piperidone to give the key intermediate 1-chloro-3-[2-oxopyrrolindin-1-yl]propanes (n=1) of formula 3or 1-chloro-3-[2-oxopiperidin-1-yl]propanes (n=2) followed by its condensation with different 1-substituted piperazines of formula 4 to get the compounds of formula 1 (formulae 2 to 4 are shown in scheme 1 of the accompanying drawings).

Another method which is the subject matter of the co-pending U.S. patent application Ser. No. 08/954,516 is the process of which starts from the condensation of 1-bromo-3-chloropropane with different 1-substituted piperazines of formula 4 to give the 1-chloro-3-(4-substituted piperazin-1-yl)propanes of formula 5 followed by their condensation with 2-pyrrolidone or 2-piperidone of formula 2 to get the compounds of formula 1.

The compounds of the present invention can be used as pharmaceutical compositions comprising compounds of the present invention with a suitable pharmaceutical career.

Preferably, these compositions are used to produce antihypertensive and antiischemic activities and contain an effective amount of the compounds useful in the method of the invention. The most preferred compound of the invention is 1-[4-(4-fluorophenyl)piperazin-1-yl]-3-[2-oxopyrrolidin-1-yl]propane.

BACKGROUND OF THE INVENTION

Hypertension is the most common of all cardiovascular diseases afflicting about 10–20% adult population. Several classes of drugs may be used in the treatment and management of hypertension such as alpha-adrenoceptor antagonists, ACE inhibitors, angiotensin I chymase inhibitors, renin inhibitors, angiotensin II antagonists, vasopressin $V_1$ antagonists, endothelin antagonists, endothelin-converting enzyme inhibitors, potassium channel activators, calcium channels antagonists, adenosine $A_2$ agonists, adenosine $A_1$ antagonists, neutral endopeptidase inhibitiors, dual-action ACE and neutral endopeptidase inhibitors.

These drugs belong to structurally diverse class of heterocyclics including substituted arylpiperazines. In this context, the 1-[4-Arylpiperazin-1-yl]-3-[2-oxopyrrolidin-1-yl]propanes and 1-[4-Arylpiperazin-1-yl]-3-[2-oxopiperidin-1-yl]propanes of the formula 1 are structurally novel compounds and show significant antihypertensive and antiischemic activities. Thus, these compounds would be useful in the treatment of hypertension and in preventing post-ischemic reperfusion injury (ischemia).

The most commonly used antihypertensive drugs are ACE's inhibitors (captopril and related drugs), $Ca^{++}$ channel blocker (nifedipine, verapamil, diltiazen) and peripheral $alpha_1$-adrenergic antagonist such as prazosin. As these drugs have one or the other side effects, there has been a continuous search for new and safe antihypertensive agents acting by these mechanism and by other novel mechanism which include mainly endothelin antagonists [Gulati, A. and Srimal, R. C. *Drug Dev. Res.*, 26, 361, 1992; Antihypertensive Drugs. *The Year's Drug News*, 145–167, 1994]. There are no drugs available to prevent post-ischemic reperfusion injury. However, the existing drugs or chemical agents like $Ca^{++}$ channel blockers [Hensch, G. *Cardiovascular Res.*, 26, 14, 1992; Karin Pazyklenk, Robert A. Kloner. *Cardiovascular Research*, 26, 82, 1992], $K_{ATP}$ openers [Allen W. Gomoll et al., *J. Pharmacol. Exp. Ther.*, 281, 24, 1997; Arthur A. M. Wilde, *Cardiovascular Research*, 35, 181, 1997] $Na^+/H^+$ exchange inhibitors [Worfgang Scholz et al., *Cardiovas. Res.*, 29, 260, 1995], have been shown to promote myocardial salvage and enhance function recovery in vivo, only when given before or during ischemic episode. However, administration of these agents only during reperfusion does not result in cardioprotective activity (Grover, G. J. et al., *Cardiovasc. Drugs Ther.*, 4, 465, 1990 & *Eur. J. Pharmacol.*, 191, 11, 1990; Mizumura, T. et al., *Circulation*, 92, 1236, 1995). Besides the use of antiischemic agents in prevention of ischemic/reperfusion injury, there is an unmet medical need for agents to treat post-ischemic reperfusion injury which may simulate the real clinical situation of myocardial infarction.

PRIOR ART

Among a large number of the molecules incorporating arylpiperazines and showing antihypertensive activity, some relevent ones are thienopyrimidine-2,4-diones of formula I of the accompanying drawings-1 (U.S. Pat. No. 4,670,560, 1989), pyrazoles of formula II of the accompanying drawings—1 (Arya, V. P. et al., *Experentia*, 23, 514, 1967), tetrazoles of formula III of the accompanying drawings—1 (Hayae, S. et al. *J. Med. Chem.*, 10, 400, 1967), prazocin analogs of formula IV of the accompanying drawings—1 (Luther, R. R. et al., *Am. Heart J.*, 117, 842, 1989; Ames, R. P. & Kiyasu, J. Y. *J. Clin. Pharmacol.*, 29, 123, 1989), 2-[3-[4-(4-fluorophenyl)piperazin-1-yl]propanes]-1,4-benzothiazin-3(4H)-one of formula V of the drawings—1 (Kajine, M. et al., *Chem. Pharm. Bull.*, 39, 2885, 1991), uracil derivatives of formula VI & VII of the accompanying drawings—1 (Klmm, Von K. et al., *Arzneim. Forsch.*, 27, 1875, 1977), dihydropyridines of formula VIII of the accompanying drawings—1 (Suzuki, H. & Saruta, T. *Cardiovasc. Drug Rev.*, 7, 25, 1989; Kubo, K. and Karasawa, A. 10*th Int. Cong. Pharmacol.*, 734, 1987; *Drugs of the Future*, 14, 291, 1989; Meguro, K. et al., *Chem. Pharm. Bull.*, 33, 3787, 1985; Nakaya, H. et al., *Eur. J. Pharmacol.*, 146, 35, 1988; Kakihand, M. et al., Jpn. *J. Pharmacol.*, 48, 223, 1988; Takenaka, T. et al., *Arzneim. Forsch.*, 26, 2127, 1976; Kajimo, M. et al., *Chem. Pharm. Bull.*, 37, 2225, 1989; Tricerri, S. Z. et al., U.S. Pat. No. 4,894,460, 1990:*Chem. Abst.*, 113, 132218b, 1990), zolertine of formula IX of the accompanying drawings—1 (Arya, V. P. et al., *Experientia*, 23, 514, 1967; Hayao, S. et al., *J. Med. Chem.*, 10, 400, 1967), thiepin derivatives of formula X of the accompanying drawings—2 (Uno, H. et al., U.S. Pat. No. 4,749,703, 1988), triazolylamine of formula XI of the accompanying drawings 1 (Mayer, W. E. et al., *J. Med. Chem.*, 32, 593, 1989), aryloxypropanolamines of formula XII of the accompanying drawings—2 (Ing, H. R. & Ormerod, W. E., *J. Pharm. Pharmacol.*, 4, 21, 1952; Petrow, V. et al., *J. Pharm. Pharinacol.*, 8, 666, 1956; Moran, N. C. and Perkins, M. E., *Pharmacol. Exp. Ther.*, 124, 223, 1958), aryloxy/thioaryloxy arylpiperazinylpropanes of formula XIII of the accompanying drawings—2 (Agarwal, S. K. et al., *Ind. J. Chem.*, 21B, 435, 1982; *Ind. J. Chem.*, 21B, 914, 1982; *Ind. J. Chem.*, 30B, 413, 1991; Rao, J. et al., *Ind. J. Chem.*, 26B, 761, 1987; Saxena, A. K. et al., *Ind. J. Chem.*, 32B, 1249, 1993), quinolylethanes of formula XIV of the accompanying drawings—2 (Murti, A. et al., *Ind. J. Chem.*, 28B, 934, 1989), trimetazidine of formula XV of the accompanying drawings—2 (Fujita, Y, Jpn. *J. Pharmacol.*, 17, 19, 1976), lidoflazine of formula XVI of the accompanying drawings—2 (Daenen, W. & Flameng, W., Angiology, 32, 543, 1981), isoquinolylmethyl derivatives of formula XVII of the accompanying drawings—2 (Nakajiza, T. et al., Arzneim-Forsch., 37, 674, 1987), dihydropyridazinone derivative of formula XVIII of the accompanying drawings—2 (Yao, F. M. et al., *Yaaxue Xuebao*, 28, 548, 1993), pyrroloquinoline derivative of formula XIX of the accompanying drawings—2 (Jasserand, D. et al., Ger. Offen. DE 4,128,015, 1993: *Chem. Abst.*, 119, 139255f, 1993).

SUMMARY OF THE INVENTION

The invention relates to a propane compound of 1-[4-arylpiperazin-1-yl]-3-[2-oxopyrrolidin-1-yl]propane or 1-[4-arylpiperazin-1-yl]-3-[2-oxopiperidin-1-yl]propane having formula I:

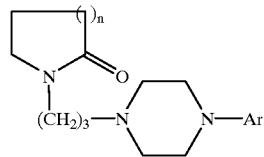

wherein Ar represents a phenyl ring substituted with halogen, alkoxy, alkyl or heteroaryl, and n=1 or n=2. In a preferred embodiment, the propane compound includes at least one of:

(a) 1-[4-(3-chlorophenyl)piperazin-1-yl]-3-[2-oxopyrrolidin-1-yl]propane;
(b) 1-[4-(4-chlorophenyl)piperazin-1-yl]-3-[2-oxopyrrolidin-1-yl]propane;
(c) 1-[4-(3-fluorophenyl)piperazin-1-yl]-3-[2-oxopyrrolidin-1-yl]propane;
(d) 1-[4-(4-fluorophenyl)piperazin-1-yl]-3-[2-oxopyrrolidin-1-yl]propane;
(e) 1-[4-(4-ethylphenyl)piperazin-1-yl]-3-[2-oxopyrrolidin-1-yl]propane;
(f) 1-[4-(2-ethylphenyl)piperazin-1-yl]-3-[2-oxopyrrolidin-1-yl]propane;
(g) 1-[4-(4-chlorophenyl)piperazin-1-yl]-3-[2-oxopiperidin-1-yl]propane;
(h) 1-[4-(3-chlorophenyl)piperazin-1-yl]-3-[2-oxopiperidin-1-yl]propane;
(i) 1-[4-(4-fluorophenyl)piperazin-1-yl]-3-[2-oxopiperidin-1-yl]propane;
(j) 1-[4-(2-ethylphenyl)piperazin-1-yl]-3-[2-oxopiperidin-1-yl]propane;
(k) 1-[4-(2-methoxyphenyl)piperazin-1-yl]-3-[2-oxopiperidin-1-yl]propane;
(l) 1-[4-(2-pyridyl)piperazin-1-yl]-3-[2-oxopiperidin-1-yl]propane; and
(m) 1-[4-(3-trifluoromethylphenyl)piperazin-1-yl]-3-[2-oxopiperidin-1-yl]propane.

In another embodiment, the invention relates to a process for the synthesis of the above compounds by condensing a substituted phenylpiperazine, wherein the substituted phenyl includes at least one of halogen, alkoxy, alkyl or heteroaryl, in the presence of an intermediate component selected from the group of 1-chloro-3-[2-oxopyrrolidin-1-yl]propane of formula 3, wherein n=1, and 1-chloro-3-[2-oxopiperidin-1-yl]propane of formula 3, wherein n=2, and a mixture thereof, and a base and an organic solvent at a temperature ranging from about 70° C. to 120° C. for between about 8 to 14 hours to produce the corresponding 1-[4-substituted arylpiperazin-1-yl]-3-[3-oxopyrrolidin-1-yl]propane or 1-[4-substituted arylpiperazin-1-yl]-3-[2-oxopiperidin-1-yl]propane of formula 1. In another embodiment, the synthesis of the intermediate component includes reacting a reactant selected from the group of 2-pyrrolidone of formula 2, wherein n=1, and 2-piperidone of formula 2, wherein n=2, with 1-bromo-3-chloropropane in the presence of at least one aromatic solvent selected from the group of xylene, toluene, a base including at least one of a pulverized sodium metal, a potassium metal, or a potassium tert. butoxide, and a mixture thereof, at a temperature of about 110° C. to 150° C. for about 80 minutes to 14 hours. In a preferred embodiment, the base is selected to include sodium carbonate or potassium carbonate. In another preferred embodiment, the condensing further includes providing a catalyst having sodium iodide or potassium iodide.

In another preferred embodiment, the molar ratio of the 1-chloro-3-[2-oxopyrrolidin-1-yl]propane to 1-chloro-3-[2-oxopiperidin-1-yl]propane in the intermediate component is about 1:1. In yet another preferred embodiment, the organic solvent includes DMF, toluene, or xylene and the organic solvent is present from about 0.8 to 2.4 ml per mmol of the intermediate component. In another preferred embodiment, the molar ratio of the base to the intermediate component is about 1:2.

The invention also relates to pharmaceutical compositions having the compound of Formula I described above in admixture with a pharmaceutically acceptable carrier. The invention further relates to a process for preparing the pharmaceutical composition by bringing the compound into association with a pharmaceutically acceptable additive.

The invention also relates to method of treating various diseases with the pharmaceutical composition of the present invention. In one embodiment, the method involves treating hypertension in mammals by administering to a patient in need thereof a therapeutically effective amount of the pharmaceutical composition. In another embodiment, the method treats peripheral vascular diseases in mammals by administering to a patient in need thereof a therapeutically effective amount of the pharmaceutical composition. In another embodiment, the method relates to antagonizing peripheral alpha-adrenergic receptors in mammals by administering to a patient in need thereof an effective amount of the composition. In yet another embodiment, the method involves treating diseases arising out of alterations in a central circulation, peripheral circulation, or adrenergic receptor system that comprises administering to a subject in need thereof a therapeutically effective amount of the composition. In a further embodiment, the method treats reperfusion injury in mammals by administering to a patient in need thereof a therapeutically effective amount of the composition. In another embodiment, the method involves treating ischemic diseases in mammals by administering to a patient in need thereof an effective amount of the composition.

In a preferred embodiment, the diseases treated are selected to be myocardial ischemia, myocardial infarction (MI), angina pectoris, cardiac surgical intervention, renal ischemia, circulatory insufficiency in extremities, stroke, trauma, or a combination thereof. In another preferred embodiment, the ischemic diseases are selected to include myocardial infraction (MI), angina pectoris, or cardiac surgical intervention. In another preferred embodiment, the halogen of the compound is selected from the group of chlorine, fluorine, bromine, and iodine, and mixtures thereof, the alkoxy is selected to be a $C_1$–$C_{10}$oxy, the alkyl is selected to be $C_1$–$C_{10}$alkyl, and the heteroaryl is selected to be a $C_4$–$C_{10}$heteroaryl.

BRIEF DESCRIPTION OF THE DRAWINGS

The present invention may be more clearly understood by reference to the following Figures.

DETAILED DESCRIPTION OF THE INVENTION

Figure 1:
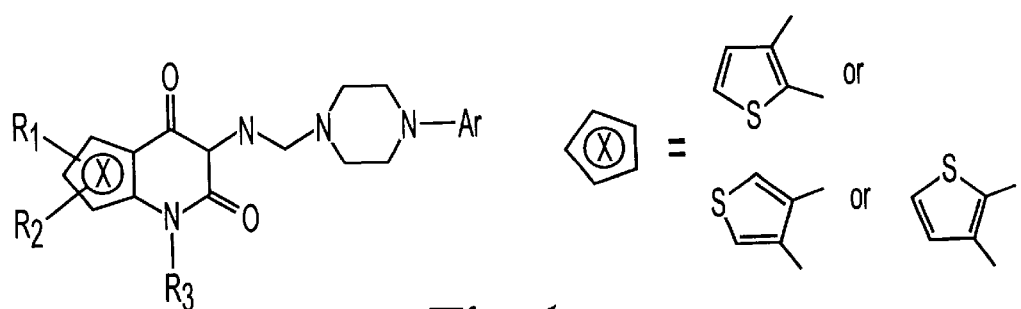
FIG. 1 illustrates prior art thienopyrimidine-2-,4-dione compounds of formula I.
Figure 2:
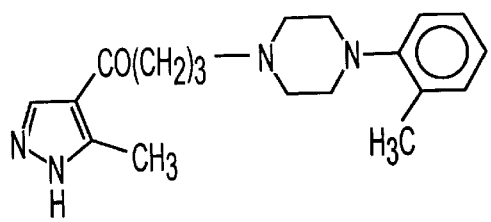
FIG. 2 illustrates prior art pyrazole compounds of formula II.
Figure 3:
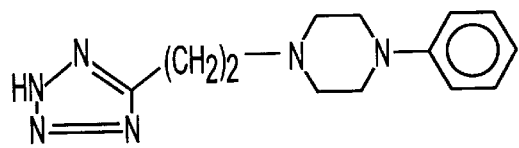
FIG. 3 illustrates prior art tetrazole compounds of formula III.
Figure 4:
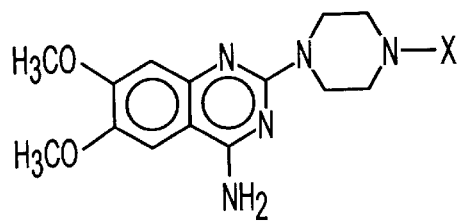
FIG. 4 illustrates prior art prazocin analog compounds of formula IV.
Figure 5:
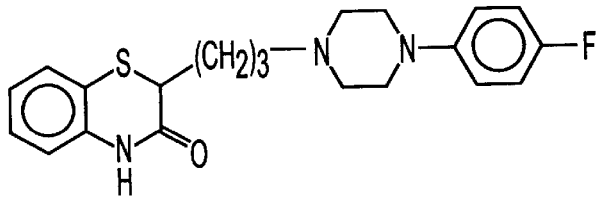
FIG. 5 illustrates prior art 2-[3-[4-(4-fluorophenyl) piperzin-1-yl]propanes]-1,4-benzothiazin-3(4H)-one compounds of formula V.
Figure 6:
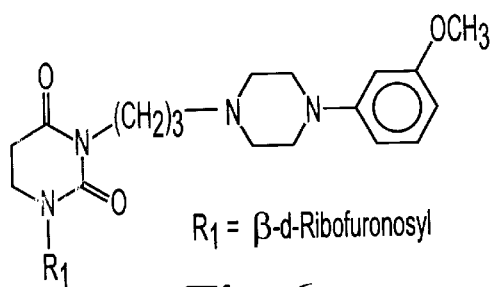
FIGS. 6 and 7 illustrate prior art uracil compounds of formulas VI and VII.
Figure 7:
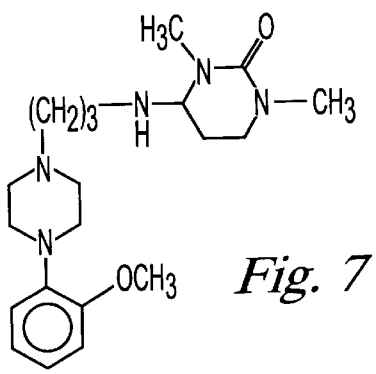
Figure 8:
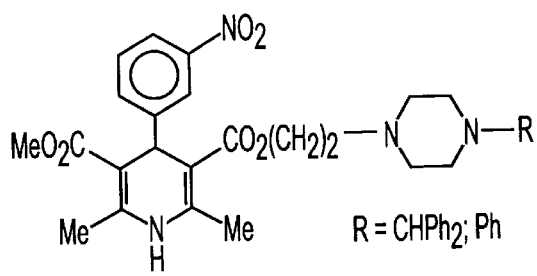
FIG. 8 illustrates prior art dihydropyridine compounds of formula VIII.
Figure 9:
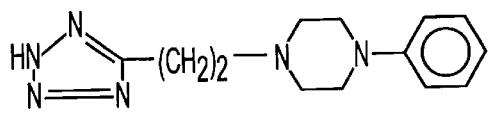
FIG. 9 illustrates prior art zolertine compounds of formula IX.
Figure 10:
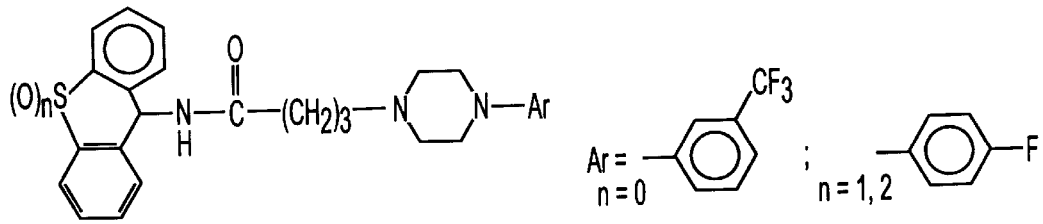
FIG. 10 illustrates prior art thiepin compounds of formula X.
Figure 11:
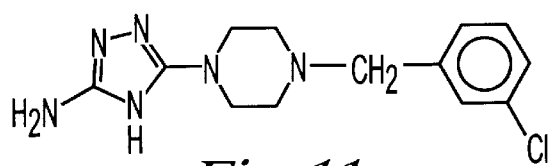
FIG. 11 illustrates prior art triazolylamine compounds of formula XI.
Figure 12:
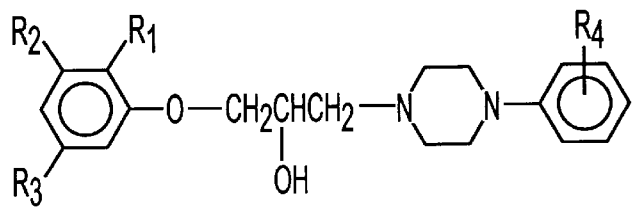
FIG. 12 illustrates prior art aryloxypropanolamine compounds of formula XII.
Figure 13:
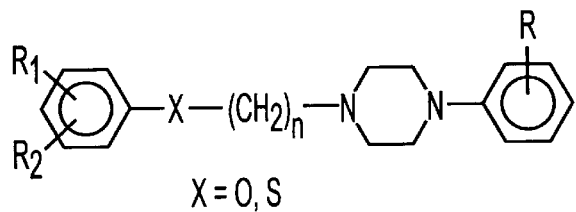
FIG. 13 illustrates prior art aryloxy and thioaryloxy arylpiperazinylpropane compounds of formula XIII.
Figure 14:
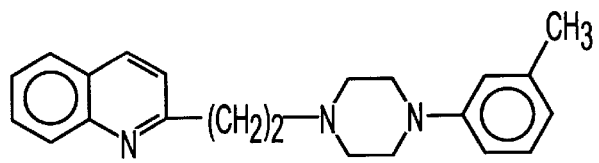
FIG. 14 illustrates prior art quinolylethane compounds of formula XIV.
Figure 15:
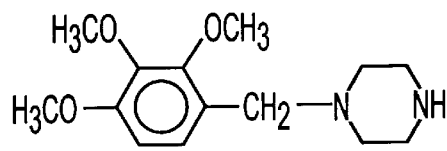
FIG. 15 illustrates prior art trimetazidine compounds of formula XV.
Figure 16:
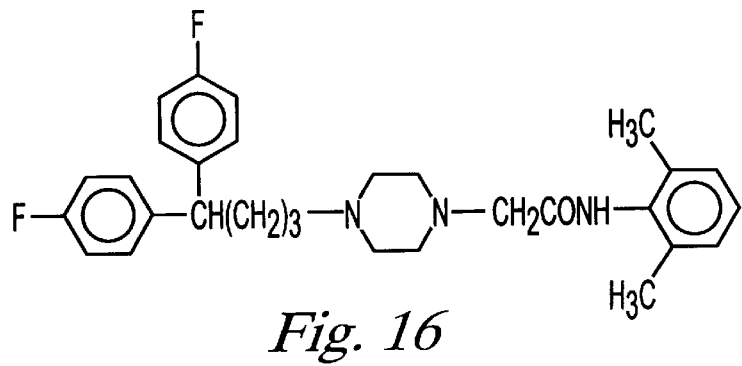
FIG. 16 illustrates prior art lidoflazine compounds of formula XVI.
Figure 17:
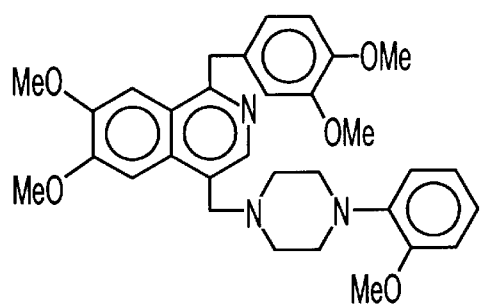
FIG. 17 illustrates prior art isoquinolylmethyl compounds of formula XVII.
Figure 18:
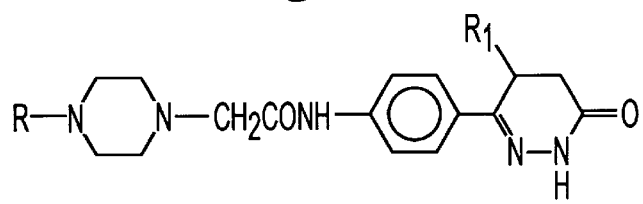
FIG. 18 illustrates prior art dihydropyridazinone derivative compounds of formula XVIII.
Figure 19:
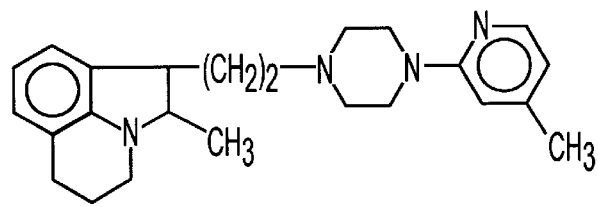
FIG. 19 illustrates prior art pyrroloquinoline derivative compounds of formula XIX.
Figure 20:
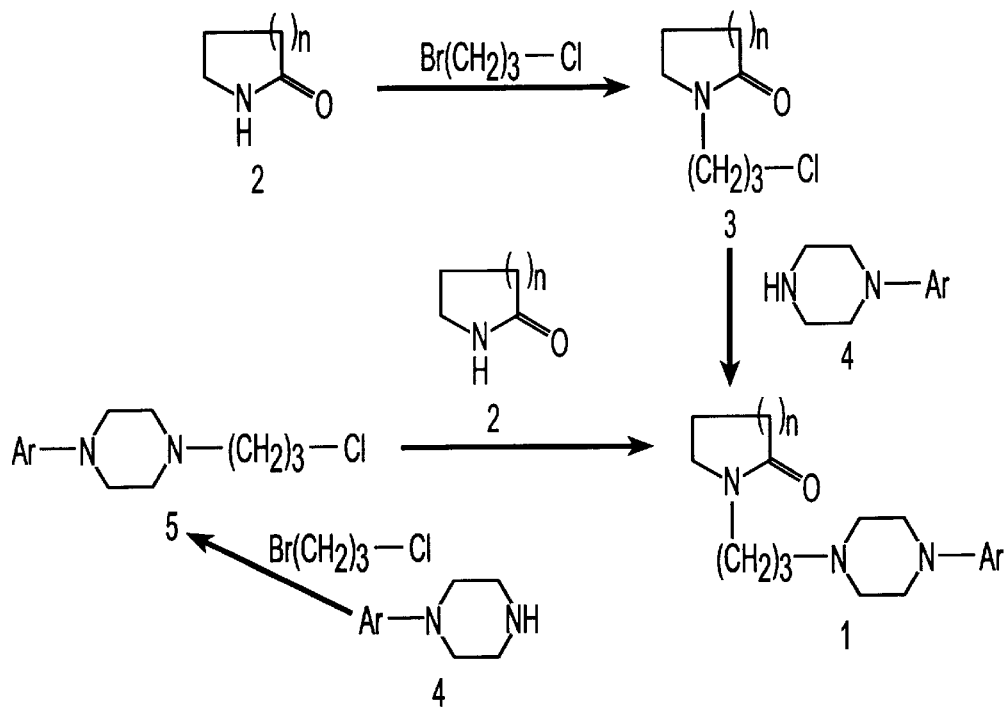
FIG. 20 illustrates the reaction sequence resulting in 1-[4-ARYLPIPERAZIN-1-YL]-3-[2-OXOPYRROLIDIN-1-YL]PROPANES and 1-[4-ARYLPIPERAZIN-1-YL]-3-[2-OXOPIPERIDIN-1-YL]PROPANES according to the present invention.

Mainly, the present invention centres around the following objects:

(i) The first object of the invention is to provide novel molecules incorporating piperazine flanked on one side by aromatic system and on the other side by 2-(oxopyrrolidin-1-yl)propanes or 2-(oxopiperidin-1-yl)propanes that exhibit better therapeutic efficacy to treat hypertension over the existing antihypertensive agents.

(ii) The second object of the invention is to provide novel 1-(4-arylpiperazin-1-yl)-3-(2-oxopyrrolidin-1-yl)propanes and 1-(4-arylpiperazin-1-yl)-3-(2-oxopiperidin-1-yl) propanes exhibiting activity against ischemic reperfusion injury for which there is no agent available t ill date to the best of the applicants knowledge.

(iii) The third object of the invention is to provide 1-(4-arylpiperazin-1-yl)-3-(2-oxopyrrolidin-1-yl)propanes and 1-(4-arylpiperazin-1-yl)-3-(2-oxopiperidin-1-yl) propanes as therapeutic agents for the diseases arising out of alterations/impairment in central/peripheral circulations and adrenergic receptors systems, such as myocardial ischemia, myocardial infarction (MI), angina pectoris, any cardiac surgical interventions, renal ischemia, circulatory insufficiency in extremities, stroke and trauma.

(iv) The fourth object of the invention is to provide a process for preparing novel 1-(4-aryl-piperazin-1-yl)-3-(2-oxopiperidin-1-yl)propanes and 1-(4-aryl-piperazin-1-yl)-3-(2-oxopiperidin-1-yl)propanes.

(v) The fifth object of the invention relates to a pharmaceutical composition comprising 1-[4-Arylpiperazin-1-yl]-3-[2-oxopyrrolidin/piperidin-1-yl]propanes and pharmaceutically acceptable additive(s) and a process for preparing such composition.

(vi) The sixth object of the invention relates to a method treating hypertension, ischemic reperfusion injury and diseases arising out of alternations/impairment in central/peripheral circulations and adrenergic receptors systems, such as myocardial, ischemia, myocardial infarction (MI), angina pectoris, any cardiac surgical interventions, renal ischemia, circulatory insufficiency in extremities, stroke and trauma.

(vii) The seventh object of the invention is for a method of treating hypertension, ischemia, cardiovascular and other adrenergic receptors related disorders in a patient such as human being and mammals.

To acheive the above and other objects, the present invention provides novel pharmacologically active substances, specifically new 1-(4-arylpiperazin-1-yl)-3-(2-oxopyrrolidin-1-yl)propanes and 1-(4-arylpiperazin-1-yl)-3-(2-oxopiperidin-1-yl)propanes which are used as potential therapeutic agents for hypertension, ischemia, cardiovascular and other adrenergic receptors related disorders.

Accordingly, the invention provides novel compounds of formula 1.

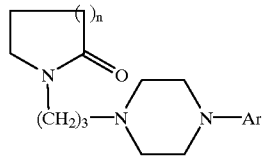

1

Wherein Ar represents a phenyl ring substituted by the groups like halo, alkoxy, alkyl or heteroaryl, n=1 or n=2 and the said compounds represented by following.

(a) 1-[4-(3-chlorophenyl)piperazin-1-yl]-3-[2-oxopyrrolidin-1-yl]propane.

(b) 1-[4-(4-chlorophenyl)piperazin-1-yl]-3-[2-oxopyrrolidin-1-yl]propane.

(c) 1-[4-(3-fluorophenyl)piperazin-1-yl]-3-[2-oxopyrrolidin-1-yl]propane.

(d) 1-[4-(4-fluorophenyl)piperazin-1-yl]-3-[2-oxopyrrolidin-1-yl]propane.

(e) 1-[4-(4-ethylphenyl)piperazin-1-yl]-3-[2-oxopyrrolidin-1-yl]propane.

(f) 1-[4-(2-ethylphenyl)piperazin-1-yl]-3-[2-oxopyrrolidin-1-yl]propane.

(g) 1-[4-(4-chlorophenyl)piperazin-1-yl]-3-[2-oxopiperidin-1-yl]propane.

(h) 1-[4-(3-chlorophenyl)piperazin-1-yl]-3-[2-oxopiperidin-1-yl]propane.

(i) 1-[4-(4-fluorophenyl)piperazin-1-yl]-3-[2-oxopiperidin-1-yl]propane.

(j) 1-[4-(2-ethylphenyll)piperazin-1-yl]-3-[2-oxopiperidin-1-yl]propane.

(k) 1-[4-(2-methoxyphenyl)piperazin-1-yl]-3-[2-oxopiperidin-1-yl]propane.

(l) 1-[4-(2-pyridyl)piperazin-1-yl]-3-[2-oxopiperidin-1-yl]propane.

(m) 1-[4-(3-trifluoromethylphenyl)piperazin-1-yl]-3-[2-oxopiperidin-1-yl]propane.

In the specification and claims, the compounds with n=1 designates 2-oxopyrrolidin-1-yl groups while with n=2 designates 2-oxopiperidin-1-yl groups. Aryl designates a pyridyl or phenyl, or a phenyl group substituted by one or more alkyl, alkoxy or halogen groups.

A preferred group of compound comprises those in which n=1 or n=2, aryl group is 2 or 4-pyridyl, phenyl, or phenyl group substituted by alkyl groups like H, $C_2H_5$, $CF_3$, alkoxy like methoxy, halo like chloro, fluoro etc. The compounds of this invention have useful biological activities and have in particular strong antihypertensive and antiischemic activities.

The invention also provides a pharmaceutical composition comprising a compound of formula 1 in admixture with a pharmaceutically acceptable conventional carriers and a process for the preparation of a pharmaceutical composition which comprises bringing a compound of the formula 1 into association with a pharmaceutically acceptable conventional carrier.

In addition, the invention provides a method of treating hypertension and peripheral viscular diseases in mammals, that comprises administering to a subject in need thereof an effective amount of a compound of formula 1. Further, the present invention is for a method of antagonising peripheral alpha-adrenergic receptor in mammals, said method comprising administering to a patient/subject in need thereof an effective amount of a compound of formula 1.

DESCRIPTION OF PREFERRED EMBODIMENTS

The reaction sequence leading to 1-[4-arylpiperazin-1-yl]-3-[2-oxopyrrolidin-1-yl]propanes or 1-[4-arylpiperazin-1-yl]-3-[2-oxopiperidin-1-yl]propanes is shown in scheme 1 of the accompanying drawings.

It will be noted that according to the foregoing scheme, there are two methods leading to the synthesis of compounds of formula 1 shown earlier.

In the first method the 2-pyrrolidone (2, n=1) or 2-piperidone (2, n=2) is condensed with 1-bromo-3-chloropropane in the presence of bases selected from potassium tert. butoxide, pulverized alkali metals selected from sodium or potassium in nonpolar solvents selected from benzene, xylene, toluene at a temperature ranging from 110 to 150° C. for 1.15 to 14 hrs to give 1-chloro-3-[2-oxopyrrolidin-1-yl]propane (3, n=1) or 1-chloro-3-[2-oxopiperidin-1-yl]propane (3, n=2) which on condensation with appropriately substituted piperazines, gave the required compounds of formula 1. This reaction may be carried out in solvents selected from acetone, methylethyl ketone, tetrahydrofuran or dimethylformamide using bases selected from triethylamine, pyridine, sodium or potassium carbonate and catalysts selected from sodium/potassium iodide to improve the yield of the compound of formula 1.

In the second method which is the subject matter of co-pending U.S. patent application Ser. No. 08/954,516 the substituted piperazine (formula 4 of scheme 1 of the accompanying drawings) was condensed with 1-bromo-3-chloropropane in presence of bases selected from sodium or potassium carbonate and catalytic amounts of sodium or potassium iodide in solvents selected from DMF, toluene, xylene etc. at a temperature ranging from 70 to 150° C. for 8 to 14 hrs to give 1-chlro-3-(4-substituted piperazin-1-yl)propane (formula 5 of scheme 1 of the accompanying drawings) which on condensation with 2-oxo-pyrrolidine or 2-oxopiperidine in presence of bases selected from potassium tert. butoxide or pulverised sodium or potassium in nonpolar solvents selected from xylene, toluene at a temperature ranging from 110 to 150° C. for 1.15 to 14 hrs yield the required compounds of formula 1.

The 1-[4-arylpiperazin-1-yl]-3-[2-oxopyrrolidin-1-yl]propanes (1 n=1) and 1-[4-arylpiperazin-1-yl]-3-[2-oxopiperidin-1-yl]propanes (1 n=2) in free form can, if desired, be converted in to their non-toxic pharmaceutically acceptable acid addition and quaternary ammonium salts. Salts which may be formed comprise, for example, salts with inorganic acids such as hydrochloride, hydrobromide, hydroiodide, sulphate and phosphate. They may also comprise salts with organic acids including mono basic acids such as acetate or propionate and especially those with hydroxy organic acids and dibasic acids such as the citrate, tartarate, malate and maleate. Among useful quaternary ammonium salts are those formed by such alkyl halides as methyl iodine and n-hexyl bromide.

The compounds of the invention show marked antihypertensive alpha-adrenergic blocking and antiischemic activities and can he used as therapeutic agents in diseases arising out of alterations/impairment in central/peripheral circulations and adrenergic receptors systems, such as myocardial ischemia, myocardial infarction (MI), angina pectoris, any cardiac surgical interventions, renal ischemia, circulatory insufficiency in extremities, stroke and trauma as shown for instance by the following data of the compound 1-[4-(4-fluorophenyl)piperazin-1-yl]-3-[2-oxopyrro-lidin-1-yl] propanes.

Pharmacological Activity

1. Acute toxicity ($LD_{50}$)
   Mice 147.0 mg/kg i.p. (C.L.=85.3–253)
   562.0 mg/kg p.o. (C.L.=383–825)
2. Effect on blood pressure, heart rate and adrenaline vasopressor response of anaesthetized (pentobarbitone sodium 40 & 60 mg/kg i.p. in cat and rat respectively) normotensive & hypertensive rat & cat model preparations.

| | Dose (uMol/kg i.d.) | B.P. Fall (%) | Heart rate (min.) | vasopressure Pre/post treatment | Adrenaline response % inhibition | No. of exp. |
|---|---|---|---|---|---|---|
| (A) CAT | | | | | | |
| (i) | Naturally occurring hypertensive cat | | | | | |
| | 10 | 16 | 110 | 195/195 | 49 | n = 4 |
| | 20 | 22 | >156.75 | 177/185 | R 26 | n = 4 |
| (ii) | Normotensive cat | | | | | |
| | 10 | 22 | 85 | 200/170 | 26 | n = 4 |
| | 20 | 21 | >102.5 | 185/165 | 34.75 | n = 4 |
| (B) RAT | | | | | | |
| (i) | Hypertensive rat model preparation | | | | | |
| | 5 | 27 | 51 | 350/370 | 33 | n = 3 |
| | 10 | 22 | 76 | 356/340 | 23 | n = 5 |
| | 20 | 29 | 100 | 310/275 | 54 | n = 1 |
| (ii) | Normotensive rat model preparation | | | | | |
| | 2 i.v. | 25 | 11 | 350/370 | +7 R22 | n = 2 |
| | 10 i.v. | 10 | 3 | 315/360 | +14 R28 | n = 2 |
| | 20 i.v. | 21 | 27.5 | 315/285 | −9.5 R42 | n = 2 | i.d. = Intraduodenal route;
R = Reversal

3. Possible Site and Mechanism of Action
(I) SITE

| | Dose (umol/kg i.d.) | B.P. fall (%) | Dur. (min.) |
|---|---|---|---|
| (i) Spinal transected cat | 2–10 | 14–18 | 15–30 |
| (ii) ICV | 0.34–1.36 | '8–10 | 10–15 |
| (iii) Rat hind limb perfusion | | | |

| Total dose (ug) | Percent change in flow |
|---|---|
| 10 | no effect |
| 25 | +35 (Vasodilation) |
| 50 | +50 (Vasodilation) |

(II) MECHANISM OF ACTION
(A) In vitro
(i) Isolated aortic strip:
Endothelin induced contraction was inhibited significantly.
Even after washing the preparation endothelin caused relaxation rather than contraction.
(ii) Isolated Guinea pig ileum preparation endothelin relaxation rather than contraction.
Compound showed significant antihistaminic activity (0.5–5.0 ug/ml).
(iii) Langendorff's perfused rat heart preparation:
Lower dose of this compound (1 ug) showed some negative chronotropic effect (30% for 10 min.) but higher doses (3–5 ug) showed less negative chronotropic effect (26 & 5% for 14 & 5 min. respectively).
(iv) Konzett and Rossler preparation:
Compound showed some antihistaminic activity against histamine induced bronchoconstriction.
(v) Rat aortic ring preparation:
NE induced contraction was inhibited by the compound.
(B) In viva Drug antagonism studies at 2 uMol dose i.v. in cat:
(i) Pretreatment with $alpha_1$-adrenergic receptor blocker, prazosin significantly (90%) reduced antihypertensive effect.
(ii) Pretreatment with Ca++ channel blocker, verapamil significantly reduced antihypertensive effect (50%).
(iii) Pretreatment with captopril (an ACE inhibitor) or Dup-753 (an angiotension Il-receptor antagonist) also reduced the antihypertensive effect (33%)

(iv) ATP sensitive potassium channel (KATP) blocker glibenclamide pretreatment only partially reduced the fall in LiHOI pressure.

(v) Pretreatment with, atropine sulphate, mepyramine maleate, propranolol, or yohimbine failed to alter the antihypertensive effect of this compound.

(4) Comparative Antihypertensive Effect With Clinically Used Antihypertensive Drugs at 2 uMol/kg i.v. Dose in Cat

| | Drug | B.P. fall (%) | Dur. (Min.) |
|---|---|---|---|
| (i) | Verapamil | 55 | 22 |
| (ii) | Captopril | 14 | 28 |
| (ii) | Compound 1 of formula 1 Ar = $C_6H_4$-4-F, where n = 1 | 22 | 25 |

(5) Cardioprotective Activity

The most interesting observation is its cardioprotective effect against myocardial stunning at a much smaller dose than antihypertensive dose. Further, in Langendorff perfused rat heart preparation subjected to even up to 90 mm. global ischemia, the compound at 0.001 ug/ml conc. given at the time of reperfusion revived normal rhythmic contraction started within 2 mm. (Table 1) and incidence of reperfusion induced arrhythmia were abolished.

TABLE 1

Compound administered at the time of reperfusion at the dose of 0.001 ug/ml on prolong period (90 min.) of ischemic insult.

| S. No. | Compound | Onset (min.) | Percentage recovery 15 min. | Percentage recovery 30 min. |
|---|---|---|---|---|
| 1. | Control[a] | 3 | 0.5 | 17.5 |
| 2. | Compound 1 of formula 1, where Ar = C6H4-4-F, n = 1 | 4 | 81.25 | 87.15 |
| 3. | Nifedipine[a] ($10^{-6}$ M) | 2.5 | 0.66 | 0.0 |

[a]Ischemic insult (45 mm.)

Comparable results for hypotensive/antihypertensive and antiischemic activities were obtained with a number of other compounds of formula 1 (Table 2 & 3).

TABLE 2

Effect on blood pressure, heart rate and adrenaline vasopressure response at anaesthetized (pentobarbitone sodium 35 mg/kg (iv) cat

| Compound of formula 1 Ar | n | Dose (umol/kg i.v.) | B.P. fall % | Dur. (min.) | Adrenaline[a] vasopressure response % inhibition |
|---|---|---|---|---|---|
| Chd 6H$_4$-4F | 1 | 2.0 | 25 | 71 | 9 |
| | | 10.0 | 31 | >112 | R |
| C$_6$H$_4$-2-C$_2$H$_5$ | 1 | 2.0 | 13 | 10 | Pt |
| | | 10.0 | 62 | 10 | — |
| C$_6$H$_4$-3-Cl | 1 | 2.0 | 25 | 20 | Pt- |
| | | 10.0 | 55 | >57 | |
| C$_6$H$_4$-3F | 1 | 2.0 | 18 | 3 | 80 |
| | | 10.0 | 32 | 30 | R |
| C$_6$H$_4$-2-OCH$_3$ | 1 | 2.0 | 19 | 19 | 47 |
| | | 10.0 | 23 | 67 | R |
| 2-Pyridyl | 1 | 2.0 | 22 | 16 | 40 |
| | | 10.0 | 40 | 43 | Pt |
| 2-Pyridyl | 2 | 2.0 | 34 | 53 | 28 |
| | | 10.0 | 42 | >71 | Pt |
| C$_6$H$_4$-4-Cl | 2 | 2.0 | 24 | 20 | 20 |
| | | 10.0 | 46 | 25 | 25 |
| C$_6$H$_4$-3-Cl | 2 | 2.0 | 27 | 9 | 33 |
| | | 10.0 | 44 | 62 | 10 |
| C$_6$H$_4$-3-CF$_3$ | 2 | 2.0 | — | — | Pt |
| | | 10.0 | 10 | Tr | 25 |
| C$_6$H$_4$-2-C$_3$H$_5$ | 2 | 2.0 | 35 | 55 | 68 |
| | | 10.0 | 20 | 63 | R |
| C$_6$H$_4$-4-F | 2 | 2.0 | 23 | 40 | 46 |
| | | 10.0 | 33 | >84 | R |

[a]R = Reversal;
Pt = potentiation (was within 20%)

TABLE 3

Compound administered at the time of reperfusion at a dose of 0.001 ug/ml on brief period (16 min.) of ischemic insult.

| Compound of formula 1 Ar | n | Onset (min.) | Percentage recovery 15 min. | Percentage recovery 30 min. |
|---|---|---|---|---|
| Control | — | 2.0 | 104.50 | 118.10[a] |
| C$_6$H$_4$-4-F | 1 | 1.5 | 81.25 | 78.12 |
| C$_6$H$_4$-2-C$_2$H$_5$ | 1 | 3.0 | 106.06 | 136.36 |
| C$_6$H$_4$-3-Cl | 1 | 1.0 | 50.00 | 88.80 |
| C$_6$H$_4$-4-C$_2$H$_5$ | 1 | 2.0 | 103.03 | 60.60 |
| C$_6$H$_4$-3-F | 1 | 2.0 | 120.00 | 180.00 |
| C$_6$H$_4$-3-Cl | 1 | 3.0 | 31.50 | 39.40 |
| C$_6$H$_4$-2-OCH$_3$ | 1 | 2.0 | 45.40 | 59.09 |
| C$_6$H$_4$-4-Cl | 1 | 1.0 | 87.50 | 120.80 |
| 2-Pyridyl | 1 | 2.0 | 47.60 | 71.40 |

[a]Arrhythmia present

The following examples are provided by the way of illustration of the present invention and should in noway be construed as a limitation thereof including the linker (propyl) between pyrrolidone/piperidone and N-arylpiperazine which may be ethyl or butyl.

EXAMPLE 1

(a) Preparation of 1-chloro-3-[2-oxopyrrolidin-1-yl]propane (i) A mixture of 2-pyrrolidone (1 g, 12.0 mmol) and finely pulverized sodium metal (0.28 g, 12.0 mmol) in dry xylene (60 ml) was heated at 110° C. with vigorous stirring, 1-bromo-3-chloropropane (1.8 g, 12.0 mmol) was added to the stirred reaction mixture after 3 hours and the heating at 110° C. was continued for 6 hours. The reaction mixture was filtered and xylene was removed under reduced pressure. The residue was distilled under reduced pressure to give 3 (n=1), B.P. 145° C./1 mm., yield 1.52 g (80%). IR (Neat) 2980, 2880, 1710, 14W), 1420, 1280, 1050. $^1$H NMR (CDCl$_3$): 1.92–2.18(m, 4H, 4' & 2-CH$_2$), 2.40(t, 2H, J=6.0 Hz, 3'-CH$_2$), 3.42(t, 4H, J=6.0 Hz, 5' & 3-CH$_2$), 3.58(t, 2H, J=6.0 Hz, 1-CH$_2$). MS: m/z 161 (M+). Mol. formula C$_7$H$_{12}$NOCl: Found: C, 51.96; H, 7.48; N, 8.61. Calcd.: C, 52.11; H, 7.45; N,8.69%.

(ii) A mixture of 2-pyrrolidone (10 g, 120.0 mmol) and finely pulverized sodium metal (2.76 g, 120.0 mmol) in dry xylene (600 ml) was heated at 150° C. with vigrous stirring. 1-Bromo-3-chloropropane (18.84 g, 120.0 mmol) was added to the stirred reaction mixture after 30 minutes and the heating at 150° C. was continued for 1 hour. The reaction mixture was filtered and xylene was removed under reduced pressure. The residue was distilled under reduced pressure to give 3 (n=1), B.P. 145° C./1 mm., yield 16.09 g (85%).

(iii) A mixture of 2-pyrrolidone (2 g, 23.0 mmol) and finely pulverized sodium metal (0.529 g, 23.0 mmol) in dry toluene (120 ml) was heated at 120° C. with vigrous stirring. 1-Bromo-3-chloropropane (3.97 g, 25.0 mmol) was added to the stirred reaction mixture after 6–7 hours and the heating at 120° C. was continued for 7 hours. The reaction mixture was filtered and toluene was removed under reduced pressure. The residue was distilled under reduced pressure to give the compound 3 ( ), B.P. 145° C./1 mm., yield 2.86 g (75%).

(iv) A mixture of 2-pyrrolidone (1 g, 12.0 mmol) and finely pulverized potassium metal (0.47 g, 12.0 mmol) in dry xyleiie (60 ml) was heated at 150° C. with vigrous stirring. 1-P,rumo-3-chloropropane (1.8 g, 12.0 mmol) was added to the stirred reaction mixture after 20 minutes and the heating at 150° C. was continued for 1 hour. The reaction mixture was filtered and xylene was removed under reduced pressure. The residue was distilled under reduced pressure to give 3 (n=1), B.P. 145 CC/i mm., yield 1.43 g (75%).

(v) A mixture of 2-pyrrolidone (1 g, 12.0 mmol) and pot<1 s~1 um tert. butoxide (1.34 g, 12.0 mmcl) in dry xylene (60 ml) was heated at 150° C. with vigrous stirring. 1-Bromo-3-chloropropalle (1.8 g, 12.0 mmcl) was added to the stirred reaction mixture after 2 hours and the heating at 150° C. was continued for 3 hours. The reaction mixture was filtered and xylene was removed under reduced pressure. The residue was distilled under reduced pressure to give 3 (n=1), B.P. 145° C./1 mm., yield 1.24 g (65%).

(b) Preparation of 1-chloro-3-(2-oxopiperidin-1-yl)propane

A mixture of 2-piperidone (1.19 g, 12.0 mmcl) and finely pulverized sodium metal (0.28 g, 12.0 mmol) in dry xylene (70 ml) was heated at 110° C. with vigorous stirring, 1-bromo-3-chloropropane (1.89 g, 12.0 mmol) was added to the stirred reaction mixture after 3 hours and the heating at 110° C. was continued for 6 hours. The reaction mixture was filtered and xylene was removed under reduced pressure. The residue was chromatographed on silica gel using hexane and chloroform as eluant to get 3 (n=2), B.P. 91° C./0.01 mm., yield 1.33 g (63.33%). IR (Neat): 3862, 3298, 2950, 2474, 2324, 1640, 1478, 1432, 1336, 1184, 1096, 754. $^1$H NMR (CDCl$_3$): 1.79–2.36(m,8H), 3.15–3.67(m,6H). MS: m/z 175 (M$^+$).

Mol. formula C$_8$H$_{14}$NOCl: Found: C, 54.90; H, 8.28; N, 8.25.

Calcd.: C, 54.69; H, 8.03; N, 7.97%.

EXAMPLE 2

(a) Preparation of 1-[4-(3-chlorophenyl)piperazin-1-yl]-3-[2-oxopyrrolidin-1-yl]propane of the Formula 1, Where Ar=C$_6$H$_4$-3-Cl, n=1

A mixture of 1-chloro-3-[2-oxopyrrolidin-1-yl]propane (1 g, 6.2 mmol), 1-(3-chlorophenyl)piperazine (1.22 g, 6.2 mmol) anhydrous Na$_2$CO$_3$ (0.33 g, 3.1 mmol) and NaI (0.093 g, 0.6 mmol) in dry DMF (5 ml) was stirred at 70° C. for 14 hrs. The reaction mixture was cooled, poured on water (20 ml) and the separated residue was extracted with CHCl$_3$ (2×25 ml). The extracts were dried over Na$_2$SO$_4$ and concentrated under reduced pressure to give 1-[4-(3-chlorophenyl)piperazin-1-yl]-3-[2-oxopyrrolidin-1-yl] propane as an oil which was purified by flash column chromatography over silica gel using chloroform as eluent, yield 1.50 g (75%) . IR (Neat): 3020, 2820, 1660, 1590, 1450, 1210, 730. $^1$H NMR (CDCl$_3$): 1.30–2.60(m, 12H, 3', 4', 2, 1 & 2×N—CH$_2$), 2.40–3.50(m, 8H, 5', 3 & 2×N—CH$_2$), 6.40–7.20(m, 4H, ArH). MS: m/z 321 (M$^+$) 323 (M+2).

Mol. Formula C$_{17}$H$_{24}$ClN$_3$O: Found: C, 63.58; H, 7.82; N,13.17.

Calcd.: C, 63.44; H, 7.52; N,13.06%.

(b) A mixture of 2-pyrrolidone (1 g, 12 mmol) and finely pulverized sodium metal (0.28 g, 12.0 mmcl) in dry toluene (60 ml) was heated at 120° C. with vigrous stirring for 6 hours, 1-[4-(3-chlorophenyl)piperazin-1-yl]-3-chloropropane (3.26 g, 12.0 mmol) was added to this reaction mixture and the reaction mixture was heated under stirring at 120° C. for 7 hour. The reaction mixture was filtered and toluene was removed under reduced pressure. The residue was chromatographed over flash silica gel using chloroform as eluent to give the title product, yield 2.65 g (70%), oil.

(c) A mixture of 1-chloro-3-[2-oxopyrrolidin-1-yl] propane (1.0 g, 6.2 mmol), 1-(3-chlorophenyl)piperazine (1.22 g, 6.2 minol), anhydrous Na$_2$CO$_3$(0.33 g, 3.1 mmol) and NaI (0.093 g, 0.6 mmcl) in dry toluene (10 ml) was stirred at 110° C. for 12 hrs. The solvent was removed at reduced pressure and residue was poured on water (20 ml). The separated residue was extracted with ethylacetate (3×20 ml), dried over Na$_2$SO$_4$ and concentrated under reduced pressure to give 1-[4-(3-chlorophenyl)piperazin-1-yl]-3-[2-oxopyrrolidin-1-yl]propane as an oil which was purified by flash column chromatography over silica gel using chloroform as eluent, yield 0.60 g (30.0%).

(d) A mixture of 1-chloro-3-[2-oxopyrrolidin-1-yl] propane (1 g, 6.2 mmcl), 1-(3-chlorophenyl)piperazine (1.22 g, 6.2 minol) anhydrous Na$_2$CO$_3$ (0.33 g, 3.1 mmol) and NaI (0.093 g, 0.6 mmcl) in dry xylene (15 ml) was stirred at 150° C. for 14 hours. The solvent was removed at reduced pressure and residue was poured on water (30 ml). The separated residue was extracted with dichloromethane (2×25 ml), dried over Na$_2$SO$_4$ and concentrated to give 1-[4-(3-chlorophenyl)piperazin-1-yl]-3-[3-oxopyrrolidin-1-yl] propane as an oil which was purified by flash column chromatography over silica gel using chloroform as fluent, yield 0.72 g (36%).

EXAMPLE 3

(a) Preparation of 1-[4-(4-chlorophenyl)piperazin-1-yl]-3-[2-oxopyrrolidin-1-yl]propane of the Formula 1, Where Ar=C$_6$H$_4$-4-Cl, n=1

A mixture of 1-chloro-3-[2-oxopyrrolidin-1-yl]propane (1 g, 6.2 mmol), 1-(4-chlorophenyl)piperazine (1.22 g, 6.2 mmol) anhydrous Na$_2$CO$_3$ (0.33 g, 3.1 mmol) and NaI (0.09 g, 0.6 mmol) in dry DMF (5 ml) was stirred at 70° C. for 12 hrs. The reaction mixture was cooled, poured on water (20 ml) and the separated residue was extracted with CHCl$_3$ (2×25 ml). The extracts were dried over Na$_2$SO$_4$ and concentrated under reduced pressure to give 1-[4-(4-chlorophenyl)piperazin-1-ylII-3-[2-oxopyrrolidiu-1-yl] propane which was purified by flash column chromatography over silica gel using chloroform as eluent, yield 1.48 g (74%), M.P. 78–80° C. IR (KBr): 3440, 2820, 1660, 1490, 1230, 1130, 810. $^1$H NMR (CDCl$_3$): 1.50–2.80 (m, 12H, 3', 4', 2, 1 & 2×N—CH$_2$), 3.00–3.60(m, 8H, 5', 3 & 2×N—CH$_2$), 6.80(d, 2H, J=9.0 Hz, ArH, o to Cl), 7.20(d, 2H, J=9.0 Hz, ArH, m to Cl). MS: m/z 321 (M$^+$) 323(M±2).

Mol. formula C$_{17}$H$_{24}$ClN$_3$O: Found: C, 63.84; H, 7.32; N,13.12.

Calcd.: C, 63.44; H, 7.52; N,13.06%.

(b) A mixture of 2-pyrrolidone (1 g, 12 mmol) and timely pulverized sodium metal (0.28 g, 12.0 mmol) in dry xylene (60 ml) was heated at 140° C. with vigrous stirring, 1-[4-(4-chlorophenyl)piperazin-1-yl]-3-chloropropane (3.26 g, 12.0 mmol) was added to the stirred reaction mixture after 30 minutes and the heating at 140° C. was continued for 1 hour. The reaction mixture was filtered and xylene was removed under reduced pressure to give 3 which was purified by flash column chromatography over silica gel using chloroform as eluent, yield 2.83 g (75%), M.P. 78–80° C.

(c) A mixture of 2-pyrrolidone (1 g, 12 mmol) and finely pulverized potassium metal (0.47 g, 12.0 mmol) in dry xylene (60 ml) was heated at 150° C. with vigorous stirring, 1-[4-(4-chlorophenyl)piperazin-1-yl]-3-chloropropane (3.26 g, 12.0 mmol) was added to the stirred reaction mixture after 20 minutes and the heating at 150° C. was continued for 1 hour. The reaction mixture was filtered and xylene was removed under reduced pressure to give 3 which was purified by flash column chromatography over silica gel using chloroform as eluent, yield 2.78 g (73.5%), M.P. 78–80° C.

(d) A mixture of 2-pyrrolidone (1 g, 12 mmcl) and timely pulverized potassium tert. butoxide (1.34 g, 12.0 mmol) in dry xylene (60 ml) was heated at 150° C. with vigrous stirring, 1-[4-(4-chlorophenyl)piperazin-1-yl]-3-chloropropane (3.26 g, 12.0 mmol) was added to the stirred reaction mixture after 2 hours and the heating at 150° C. was continued for 4 hour. The reaction mixture was filtered and xylene was removed under reduced pressure to give 3 which was purified by flash column chromatography over silica gel using chloroform as eluent, yield 2.46 g (65%), M.P. 78–80° C.

EXAMPLE 4

(a) Preparation of 1-[4-(3-fluorophenyl)piperazin-1-yl)-3-[2-oxopyrrolidin-1-yl]propane of the Formula 1, Where Ar=$C_6H_4$-3-F, n=1

A mixture of 1-chloro-3-[2-oxopyrrolidin-1-yl]propaur (1 g, 6.2 mmol), 1-(3-fluorophenyl)piperazine (1.12 g, 6.2 mmol), anhydrous $K_2CO_3$ (0.434 g, 3.1 mmol) and KI (0.10 g, 0.6 mmol) in dry DMF (5 ml) was stirred at 90° C. for 12 hrs. The reaction mixture was cooled, poured on water (25 ml) and the separated residue was extracted with $CHCl_3$ (2×25 ml). The extracts were dried over $Na_2SO_4$ and concentrated under reduced pressure to give 1-[4-(3-fluorophenyl)piperazin-1-yl]-3-[2-oxopyrrolidin-1-yl] propane as an oil which was purified by flash column chromatography over silica gel using chloroform as eluent, yield 1.32 g (69.6%). IR(Neat): 2920, 2800, 1650, 1440, 1240, 1150, 740. $^1$H NMR ($CDCl_3$): 1.50 –2.70(m, 12H, 3', 4', 2, 1 & 2×N—$CH_2$), 3.00–3.60(m, 8H, 5', 3 & 2×N—$CH_2$), 6.30–6.80(m, 4H, ArH). MS: m/z 305 ($M^+$) 307 (M+2).

Mol. formula $C_{17}H_{24}FN_3O$: Found: C, 67.22; H, 7.72; N, 13.97.

Calcd.: C, 66.88; H, 7.92; N, 13.76%.

(b) A mixture of 2-pyrrolidone (1 g, 12 mmol) and tinely pulverized sodium metal (0.28 g, 12.0 mmol) in dry xylene (60 ml) was heated at 150° C. with vigorous stirring, 1-[4-(3-fluorophenyl)piperazin-1-yl]-3-chloropropane (3.07 g, 12.0 mmol) was added to the stirred reaction mixture and the heating at 150° C. was continued for 1 hour. The product was obtained by the similar method as in example 3, yield 2.94 g(82%), oil.

EXAMPLE 5

(a) Preparation of 1-[4-(4-fluorophenyl)piperazin-1-yl]-3-[2-oxopyrrolidin-1-yl]propane of the Formula 1, Where Ar=$C_6H_4$-4-F, n=1

A mixture of 1-chloro-3-[2-oxopyrrolidin-1-yllpropaxie (4 g, 25.0 mmol), 1-(4-fluorophenyl)piperazine (4.47 g, 25.0 mmol), anhydrous $Na_2CO_3$ (1.325 g, 12.5 mmol) and NaI (0.38 g, 2.5 mmol) in dry DMF (20 ml) was stirred at 120° C. for 8 hrs. The reaction mixture was cooled, poured on water (30 ml) and the separated residue was extracted with $CHCl_3$ (2×30 ml). The extracts were dried over $Na_2SO_4$ and concentrated under reduced pressure to give 1-[4-(4-fluorophenyl)piperazin-1-yl]-3-[2-oxopyrrolidin-1-yl]-propane as an oil which was purified by flash column chromatography over silica gel using chloroform as eluent, yield 5.72 g (75.5%). IR (Neat): 2920, 2820, 1660, 1500, 1250, 730. $^1$H NMR ($CDCl_3$): 1.50–2.80(m, 12H, 3', 4', 2, 1 & 2×N—$CH_2$), 3.00–3.60(m, 8H, 5', 3 & 2×N—$CH_2$), 6.70–7.10(m, 4H, ArH). MS: m/z 305 ($M^+$).

Mol. formula $C_{17}H_{24}FN_3O$: Found: C, 66.55; H, 8.07; N, 13.69.

Calcd.: C, 66.86; H, 7.92; N, 13.76%.

(b) A mixture of 2-pyrrolidone (3 g, 35 mmol) and finely pulverized sodium metal (0.81 g, 35.0 mmol) in dry xylene (180 ml) was heated at 150° C. with vigrous stirring, 1-[4-(4-fluorophenyH,piperazin-1-yl]-3-chloropropane (8.96 g, 35.0 mmol) was added to the stirred reaction mixture after 30 minutes and the heating at 150° C. was continued for 1 hour. The reaction mixture was filtered and xylene was removed under reduced pressure to give 3 which was purified by flash column chromatography over silica gel using chloroform as eluent, yield 9.15 g (85%), oil.

EXAMPLE 6

(a) Preparation of 1-[4-(4-ethylphenyl)piperazin-1-yl]-3-[2-oxopyrrolidin-1-yl]propane of the Formula 1, Where Ar=$C_6H_4$-4-$C_2H_5$, n=1

A mixture of 1-chloro-3-[2-oxopyrrolidin-1-yl]propane (2.0 g, 12.0 mmol), 1-(4-ethylphenyl)piperazine (2.36 g, 12.0 mmol), anhydrous $Na_2CO_3$ (0.658 g, 6.2 mmol) and NaI (0.18 g, 1.2 mmol) in dry DMF (10 ml) was stirred at 80° C. for 12 hrs. The reaction mixture was cooled, poured on water (30 ml) and the separated residue was extracted with $CHCl_3$ (2×30 ml). The extracts were dried over $Na_2So_4$ and concentrated under reduced pressure to give 1-[4-(4-ethylphenyl)piperazin-1-yl]-3-[2-oxopyrrolidin-1-yl] propane as an oil which was purified by flash column chromatography over silica gel using chloroform as eluent, yield 2.43 g (62.0%). IR (Neat): 2940, 2800, 1660, 1440, 1000, 900,800. $^1$H NMR ($CDCl_3$): 1.20(t, 3H, J=6.0 Hz, $CH_2CH_3$), 1.60–280(m, 14H, 3',4',2,1 & 2×N—$CH_2$, $CH_2CH_3$), 3.00–3.60(m, 8H, 5', 3 & 2×N—$CH_2$). MS: m/z 315 ($M^+$).

Mol. formula $C_{19}H_{29}N_3O$: Found: C, 71.91; II, 9. 16; N, 13. 15.

Calcd.: C, 72.34; H, 9.27; N, 13.32%.

(b) A mixture of 2-pyrrolidone (2 g, 24 mmol) and finely pulverized sodium metal (0.56 g, 24.0 mmcl) in dry xylene (120 ml) was heated at 150° C. with vigrous stirring, 1-[4-(4-ethylphenyl)piperazin-lyl]-3-chloropropane (6.38 g, 24.0 mmol) was added to the stirred reaction mixture after 30 minutes and the heating at 150° C. was continued for 1 hour. The product was obtained by the similar method as in example 3, yield 6.42 g (78%), oil.

EXAMPLE 7

(a) Preparation of 1-[4-(2-ethylphenyl)piperazin-1-Yl]-3-[2-oxopyrrolidin-1-yl]propane of the Formula 1, Where Ar=$C_6H_4$-2-$C_2H_5$, n=1

A mixture of 1-chloro-3-[2-oxopyrrolidin-1-yl]propane (2.0 g, 12.0 mmol), 1-(2-ethylphenyl)piperazine (2.36 g, 12.0 mmol), anhydrous $Na_2CO_3$ (0.658 g, 6.2 mmol) and NaI (0.18 g, 1.2 mmol) in dry DMF (10 ml) was stirred at 80° C. for 12 hrs. The reaction mixture was cooled, poured on water (30 ml) and the separated residue was extracted with CHCl₃ (2×20 ml). The extracts were dried over Na₂So₄ and concentrated under reduced pressure to give 1-[4-(4-ethylphenyl)piperazin-1-yl]-3-[2-oxopyrrolidin-1-yl]propane as an oil which was purified by flash column chromatography over silica gel using chloroform as eluent, yield 2.17 g (60.0%). IR (Neat): 2940, 2820, 1660, 1430, 1010, 900, 800. $^1$H NMR (CDCl₃): 1.24(t, 3H, J=6 Hz, CH₂—CH₃), 1.68–1.85(m, 2H, 4'-CH₂), 1.98–2.10(m, 2H, 2-CH₂), 2.34–2.50(m, 4H, 3' & 1-CH₂), 2.62(bs, 4H, 2×N× CH₂), 2.68(q, 2H, CH₃—CH₂), 2.94(t, 4H, J=G.0 Hz, 2×N—CH₂), 2.35(t, 2H, ,J=6.0 Hz, 3-CH₂), 3.42(t, 2H, J=6.0 Hz. 5'-CH₂), 7.00–7.28(m, 4H, Ar-H). MS: m/z 315 (M⁺).

Mol. formula C₁₉H₂₉N3O: Found: C, 72.64; H, 9.11; N, 13.64.

Calcd.: C, 72.34; H, 9.27; N, 13.32%.

(b) A mixture of 2-pyrrolidone (1 g, 12 mmol) and tinely pulverized sodium metal (0.28 g, 12.0 mmol) in dry xylene (60 ml) was heated at 150° C. with vigorous stirring, ethylphenyl)piperazin-1-yl]-3-chloropropane (3.19 g, 12.0 mmcl) was added to the stirred reaction mixture after 30 minutes and the heating at 150° C. was continued for 1 hour. The product was obtained by the similar method as in example 3, yield 3.13 g (76%), oil.

EXAMPLE 8

(a) Preparation of 1-[4-(4-chlorophenyl)piperazin-1-yl]-3-[2-oxopiperidin-1-yl]propane of the Formula 1, Where Ar=C₆H₄-4-Cl, n=2

A mixture of 2-piperidone (1 g, 10 mmol) and finely pulverized sodium metal (0.23 g, 10 mmol) in dry xylene (60 ml) was heated at 140° C. with vigorous stirring, 1-[4-(4-chlorophenyl)piperazin-1-yl]-3-chloropropane (2.72 g, 10 mmol) was added to the stirred reaction mixture after 30 minutes and the heating at 140° C. was continued for 1 hour. The reaction mixture was filtered and xylene was removed under reduced pressure to give 3 which was purified by flash column chromatography over silica gel using chloroform as eluent, yield 2.54 g (75%) , m.p. 106° C. IR (Neat): 3761, 3408, 3017, 2957, 2882, 2826, 2785, 2502, 1659, 1599, 1499, 1456, 1385, 1346, 1219, 1148, 1105, 760, 667. PMR (CDCl₃): 0.89–1.80(m, 6H, 4',5'& 2-CH₂), 2.33–2 .65(m, 8H, 3',1 & 2×N—CH₂), 3.1573.62(m, 8H, 6',3 & 2×N (CH₂), 6.81 7.00(2×dd,4×ArH). MS: m/z 337 (M⁺2).

Mol. formula C₁₈H₂₆N₃OCl: Found: C, 64.23; H, 7.87; N, 12.24

Calcd.: C, 64.37; H, 7.80; N,12.51%.

(b) A mixture of 2-piperidone (1.0 g, 10 mmol) and tiliely pulverized potassium tert. butoxide (1.12 g, 10 mmol) in dry xylene (60 ml) was heated at 150° C. with vigrous stirring, 1-[4-(4-chlorophenyl)piperazin-1-yl]-3-chloropropane (2.72 g, 10 mmol) was added to the stirred reaction mixture after 2 hours and the heating at 150° C. was continued for 4-hour. The reaction mixture was filtered and xylene was removed under reduced pressure to give 3 which was purified by flash column chromatography over silica gel using chloroform as eluent, yield 2.17 g (64%) m.p. 106° C.

EXAMPLE 9

Preparation of 1-[4-(3-chlorophenyl)piperazin-1-yl]-3-[2-oxopiperidin-1-yl]propane of the Formula 1, Where Ar=C₆H₄-3-Cl, n=2

A mixture of 2-piperidone (1.0 g, 10 mmol) and finely pulverized sodium metal (0.23 g, 10 mmol) in dry toluene (60 ml) was heated at 120° C. with vigrous stirring for 6 hours, 1[4-(3-chlorophenyl)piperazin-1-yl]-3-chloropropane (2.72 g, 10 mmol) was added to this reaction mixture and the reaction mixture was heated under stirring at 1200 £ for 7 hour. The reaction mixture was filtered and toluene was removed under reduced pressure. The residue was chromatographed over flash silica gel using chloroform as eluant to give 3, yield 2.59 g (76.5%), oil. IR (Neat): 3406, 2951, 2878, 1626, 1597, 1491, 1454, 1383, 1352, 1219, 1142, 1103. $^1$H NMR (CDCl₃): 1.17–1.84(m, 6H, 2, 4' & 5'-CH₂), 2.27–2.65(m, 8H, 1, 3' & 2×N—CH₂), 3.15–3.37 (m, 8H, 6', 3 & 2×N—CH₂), 6.68–6.79(dd, 2×ArH), 7.05–7.11(t, 1×ArH), 7.19(s, 1×ArH). MS: m/z 335 (M⁺).

Mol. formula C₁₈H₂₆N₃OCl: Found: C, 64.17; H., 7.92; N, 12.21

Calcd.: C, 64.37; H, 7.80; N, 12.51%.

EXAMPLE 10

(a) Preparation of 1-[4-(4-fluorophenyl)piperazin-1-yl]-3-[2-oxopiperidin-1-yl]propane of the Formula 1, Where Ar=C₆H₄-4-F, n=2

A mixture of 2-piperidone (2 g, 20 mmol) and finely pulverized sodium metal (0.46 g, 20 mmcl) in dry xylene (120 ml) was heated at 150° C. with vigorous stirring, 1-[4-(4-fluorophenyl)piperazin-1-yl]-3-chloropropane (5.17 g, 20 mmol) was added to the stirred reaction mixture after 30 minutes heating at 150° C. was continued for 1 hour. The reaction mixture was filtered and xylene was removed under reduced pressure to give 3 which was purified by flash column chromatography over silica gel using chloroform as eluant, yield 4.64 g (72%), oil. IR (Neat): 3408, 3014, 2931, 2880, 2825, 1626, 1508, 1458, 1219, 824, 760, 667. $^1$H NMR (CDCl₃): 1.72–1.86(in, 6H, 4', 5' & 2-CH₂), 2.37–2.69 (m, 8H, 3', 1 & 2×N—CH₂), 3.12–3.46(m, 8H, 6', 3 & 2×N—CH₂), 6.83–7.00(2×dd,4×ArH). MS:319 (M⁺).

Mol. formula C₁₉H₂₆N₃OF: Found: C, 71.23; H, 8.26; N, 12.95

Calcd.: C, 71.47; H, 8.15; N, 13.17%.

(b) A mixture of 1-chloro-3-[2-oxopiperidin-yl]propane (2.1 g, 12 mmol), 1-(4-fluorophenyl)piperazine (2.16 g, 12 mmol), anhydrous Na₂CO₃ (0.618 g, 6.2 mmol) and Nal (0.18 g, 1.2 mmol) in dry DMF (10 ml) was stirred at 800£ for 14 hrs. The reaction mixture was cooled, poured on water (30 ml) and the separated residue was extracted with CHCl₃ (2×35 ml). The extracts were dried over Na₂SO₄ and concentrated under reduced pressure to give 1-[4-(4-fluorophenyl)piperazin-1-yl]-3-[2-oxopiperidin-1-yl]propane as an oil which was purified by column chromatography over silica gel using chloroform as eluent, yield 2.40 g (63.0%).

EXAMPLE 11

Preparation of 1-[4-(2-ethylphenyll)piperazin-1-yl]-3-[2-oxopiperidin-1-yl]propane of the Formula 1, Where Ar=C₆H₄-2-C₂H₅, n=2

A mixture of 2-piperidone (1.0 g, 10 mmol) and finely pulverized sodium metal (0.23 g, 10 mmol) in dry xylene (60 ml) was heated at 150° C. with vigorous stirring, ethylphenyl)piperazin-1-yl]-3-chloropropane (2.66 g, 10 mmol.) was added to the stirred reaction mixture after 30 minutes and the heating at 150° C. was continued for 1 hour. The react ion mixture was filtered and xylene was removed tinder reduced pressure to give 3 which was purified by flash column chromatography on silica gel using chloroform as eluant, yield 2.49 g (75%) , oil. IR (Neat): 3680, 3440, 3000, 2960, 2870, 2820, 1620, 1490, 1450, 1350, 1210, 1140, 1005, 920, 725. $^1$H NMR (CDCl₃): 1.00(t, 3H, CH₂CH₃), 1.20–1.90(m, 6H, 4', 5' & 2-CH₂), 2.20–3.50(m, 18H, 3', 6', 3, 1 & 4×N—CH2, CH₂CH₃), 7.00–7.20(m, 4H, ArH). MS: m/z 329 (M⁺).

Mol. formula C₂₀H₃₁N₃: Found: C, 72.67; H, 9.60; N, 12.49.

Calcd: C, 72.95; H, 9.42; N, 12.77%.

EXAMPLE 12

Preparation of 1-[4-(2-methoxyphenyl)piperazin-1-yl]-3-[2-oxopiperidin-1-yl]propane of the Formula 1, Where Ar=C6H5-2-OCH$_3$, n=2

A mixture of 2-piperidone (1.0 g, 10 mmol) and finely pulverized potassium metal (0.40 g, 10 mmol) in dry xylene (60 ml) was heated at 150 C. with vigrous stirring, 1-[4-(2-methoxyphenyl)piperazin-1-yl]-3-chloropropane (2.52 g, 10 mmol) was added to the stirred reaction mixture after 20 minutes and the heating at 150° C. was continued for 1 hour. The reaction mixture was filtered and xylene was removed under reduced pressure to give 3 which was purified by flash column chromatography over silica gel using chloroform as eluant, yield 2.41 g (72%), oil. IR (Neat): 2945, 1626, 1500, 1460, 1242, 908, 735, 648. PMR (CDCl$_3$): 1.69–1.84(m, 611, 4', 5' & 2-CH$_2$), 2.26–2.70(m, 8H, 3', 1 & 2×N—CH$_2$), 3.07–3.36(m, 8H, 6', 3 & 2×N—CH$_2$), 3.75(s, 3H, OCH$_3$), 6.7614 6.95(m, 4H, ArH). MS: m/z 331(M$^+$).

Mol. formula $C_{19}H_{29}N_{3O2}$: Found: C, 68.61; H, 8.92; N, 12.56

Calcd.: C, 68.85; H, 8.81; N, 12.68%.

EXAMPLE 13

Preparation of 1-[4-(2-pyridyl)piperazin-1-yl]-3-[2-oxopiperidin-1-yl]propane of the Formula 1, Where Ar=2-pyridyl, n=2

A mixture of 2-piperidone (2 g, 20 mmol) and finely pulverized sodium metal (0.46 q, 20 mmol) in dry xylene (ml) was heated at 150° C. with vigorous stirring, 1[4-(pyridyl)piperazine-1-yl]-3-chloropropane (4.78 g, 20 mmol) was added to the reaction mixture after 30 minutes and the heating at 150° C. was continued for 1 hour. The reaction mixture was filtered and xylene was removed under reduced pressure to give 3 which was purified by flash column chromatography over silica gel using chloroform as eluant, yield 4.39 g (72%), oil. IR (Neat): 3420, 2940, 2800, 1629, 1580, 1470, 1420, 1230, 1150, 1125, 960, 760. $^1$H NMR (CDCl$_3$): 1.50–2.20(m, 6H, 4', 5' & 2-CH$_2$), 2.25–2.80 (m, 8H, 3', 1 & 2×N—CH$_2$), 3.10–4.80(m, 8H, 6', 3 & 2×N—CH$_2$), 6.48–6.75(m, 2H, 3,5-pyridyl H), 7.40(m,1H, 4-pyridyl H), 8.15(m, 1H, 6-pyridyl H). MS: m/z 302 (M$^+$).

Mol. formula $C_{17}H_{26}N_4O$:Found: C, 67.32; 11, 8.49; N, 18.38

Calcd.: C, 67.52; 11, 8.67; N, 18.53%.

EXAMPLE 14

Preparation of 1-[4-(3-trifluoromethylphenyl)piperazin-1-yl]-3-[2-oxopiperidin-1-yl]propane of the Formula 1, Where Ar=C$_6$H$_4$-3-CF$_3$, n=2

A mixture of 2-piperidone (1.0 g, 10 mmol) and finely fulverized sodium metal (0.23 g, 10 mmol) in dry xylene (60 ml) was heated at 150° C. with vigorous stirring, 1-[4-(3-CF$_3$-phenyl)piperazin-1-yl]-3-chloropropane (3.06 g, 10 mmol) was added to the stirred reaction mixture after 30 minutes and the heating at 150° C. was continued for 1 hour. The reaction mixture was filtered and xylene was furnished by flush column chromatography on silica gel using CHC13 as eluant, yield 2.80 g (75%) , oil. IR (Neat): 3402, 3015, 2951, 2880, 2827, 2785, 1622, 1449, 1450, 1352, 1315, 1217, 1167, 1126, 1076, 997, 951. $^1$H NMR (CDCl$_3$): 1.75–1.93(m, 6H, 4', 5' & 2-CH$_2$), 2.35–2.75(m, PH, A,1 & 2×N—CH$_2$), 3.310–3.84(m, 8H, 61, 3 & 2×N—CH$_2$), 7.04–7.10(dd, 2H, 4, 6-ArH), 7.26(s, H, 2-ArH), 7.32–7.37 (t, H, 5-ArH). MS: m/z 369(M$^+$).

Mol. formula $C_{16}H_{26}N_3OF_3$: Found: C, 61.48; H, 7.23; N,11.21.

Calcd.: C, 61.79; H, 7.05; 11.38%.

EXAMPLE 15

Antihypertensive/Hypotensive Activity (a) Cats (2.6–4.0 kg) of either sex anaesthetized with pentobarbitone sodium (40 mg/kg i.v.) and showing basal mean arterial blood pressure below 150 mm (Hg) were categorised as normotensive and above 150 mm Hg as hypertensive. Arterial blood pressure (EP) was recorded from one of the carotid artery through a stathum P23 DC pressure transducer and 7P1 low level DC preamplifier on a Grass Model P7 Polygraph, Signals from 7P1 preamplifier were used to trigger 7P4 Tachograph preamplifier for recording the heart rate (HR). Right femoral vein and Trachea were cannulated for intravenous injections and artificial ventilation respectively. Control responses to intravenous injection of noradrenaline (2–4 ug); acetyl choline (1–2 ug); histamine (1–2 ug) and isoprenaline (1–2 ug) were taken before and after the administration of test doses of each compounds. All the compounds were tested at fixed doses of 2.0 and 10 uM/kg i.v. Significant results are given in Table 2.

(b) Antihypertensive activity was observed in naturally hypertensive cats, rat abdominal aorta coarctation model of hypertension (Liu, J; Bishop, S. P. & Overbeck, H. W. Morphometric evidence for non pressure related arterial wall thickening in hypertensiol Circ. Res. 62, 1001–1010, 1988) and L-NAME (No synthase inhibitor) induced hypertensive cats.

EXAMPLE 16

Cardioprotective/Antiischemic Activity

The rats were killed by decaptitation, heart were rapidly excised and placed in ice-cold HEPES tyrode buffer. Then isolated hearts were perfused retrogradely through coronary arteries using the Langendorff technique. The perfusion buffer consisted (in mM) NaCl 137, KCl 5.4, CaCl$_2$ 1.8, MgCl$_2$ 1.0, glucose 11.2 and HEPES 3.0. The buffer (pH 7.4) was continuously gassed with oxygen and maintained at 37° C. Coronary flow rate was maintained at 10 ml/min. The heart contracted spontaneously.

The perfused heart was allowed to equilibrate for 30 min. before initiation of any insult protocol. The test compounds were given at the time of reperfusion. Some of the compounds were dissolved in ethanol. Final concentration of ethanol in the perfusion buffer was 0.0001% and had no effect of its own on the parameter used.

(a) For brief period of ischemic insult (Hideo er al. Pathophysiology and pathogenesis of stunned myocardiitn. *J. Clin. Invest.*, 79, 950–961, 1987). Ischemia was initiated by stopping the flow for 16 min. followed by 30 min. reperfusion period. The durations were decided on the initial pilot experiments leading to 50% recovery of function.

(b) For prolong period of ischemic insult (Becker, L. C. & Ambrosio, G. Myocardial consenquences of reperfusion. Prog. *Cardiovas. Dis.*, 30, 23–44, 1987). Ischemia was initiated by stopping the flow for 30 min. followed by 30 min. reperfusion.

What is claimed is:

1. A process for the synthesis of 1-[4-arylpiperazin-1-yl]-3-[2-oxopyrrolidin-1-yl]propane or 1-[4-arylpiperazin-1-yl]-3-[2-oxopiperidin-1-yl]propane represented by formula I:

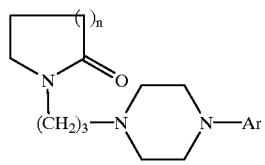

wherein Ar represents a pyridyl ring or a phenyl ring substituted with a halogen, alkoxy, alkyl, and n=1 or n=2; which comprises condensing a pyridyl piperazine or an aryl piperazine, wherein the aryl group is a phenyl ring substituted with a halogen, alkoxy, or alkyl group, with an intermediate selected from the group consisting of 1-chloro-3-[2-oxopyrrolidin-1-yl]propane and 1-chloro-3-[2-oxopiperidin-1-yl]propane in the presence of a base, a catalyst and an organic solvent to produce the desired propane compound.

2. The process recited in claim 1 wherein the synthesis of the intermediate component comprises reacting 2-pyrrolidone or 2-piperidone with 1-bromo-3-chloropropane in the presence of at least one aromatic solvent selected from the group consisting of xylene, toluene, and benzene; and a base comprising at least one of a pulverized sodium metal, a potassium metal, potassium tert. butoxide.

3. The process recited in claim 1 wherein the base is at least one of sodium carbonate or potassium carbonate.

4. The process recited in claim 1 wherein the condensing further comprises providing a catalyst that is at least one of sodium iodide or potassium iodide.

5. The process of claim 1 wherein the molar ratio of the 1-chloro-3-[2-oxopyrrolidin-1-yl]propane to 1-chloro-3-[2-oxopiperidin-1-yl]propane in the intermediate component is about 1:1.

6. The process of claim 1 wherein the organic solvent is present from about 0.8 to 2.4 mL per mmol of the intermediate component.

7. The process of claim 1 wherein the molar ratio of the base to the intermediate component is about 1:2.

8. The process of claim 1, which further comprises converting the compound to a pharmaceutically acceptable salt thereof.

* * * * *